(12) United States Patent
Sankarasubbier et al.

(10) Patent No.: US 7,112,705 B2
(45) Date of Patent: Sep. 26, 2006

(54) PROCESS FOR PREPARING ALKYLATED DIHYDROXYBENZENE

(75) Inventors: Narayanan Sankarasubbier, Andhra Pradesh (IN); Palaniappan Srinivasan, Hyderabad (IN); Katravulapalli Veera Venkata Satya Bhaskara Sita Rama Murthy, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/032,890

(22) Filed: Dec. 26, 2001

(65) Prior Publication Data

US 2003/0125586 A1    Jul. 3, 2003

(51) Int. Cl.
*C07C 37/11* (2006.01)
(52) U.S. Cl. ...................................... 568/766
(58) Field of Classification Search ................. 568/766
See application file for complete search history.

(56) References Cited

U.S. PATENT DOCUMENTS 2,722,556 A * 11/1955 Young
3,965,039 A    6/1976 Chaplits et al. ............. 252/426
4,323,715 A *  4/1982 Engel
5,072,054 A * 12/1991 Marler

FOREIGN PATENT DOCUMENTS

FR    2104085    4/1972
GB    761613     11/1956 ........................ 2/3

OTHER PUBLICATIONS

Yoo, Applied Catalysis A: General, vol. 187, pp. 225-232 (1999).*
"Montmorillonite as a versatile solid acid catalyst for tert-butylation of resorcinol", Narayanan et al., Applied Catalysis A: General 213 (2001) 273-278.

* cited by examiner

*Primary Examiner*—Elvis O. Price
(74) *Attorney, Agent, or Firm*—Morgan & Finnegan, LLP

(57) ABSTRACT

The present invention relates to a process for the preparation of alkylated dihydroxybenzene by alkylating dihydroxy benzene with tertiary butyl alcohol in the presence of a solid acid/solid polymer catalyst.

4 Claims, No Drawings

PROCESS FOR PREPARING ALKYLATED DIHYDROXYBENZENE

FIELD OF THE INVENTION

The present invention relates to a process for preparing alkylated dihydroxybenzene. More particularly, the present invention relates to a process for the preparation of alkylated dihydroxy benzene which is of use as antioxidant, polymer stabilisers, and in the treatment of mitochondrial respiration ailments, by the alkylation of dihydroxy benzene over solid acid or polyaniline sulfate as catalyst in the presence of a tertiary butyl alcohol.

BACKGROUND OF THE INVENTION

Friedel Crafts catalysis is one of the major industrially important processes that is widely used in the synthesis of low and high volume chemicals. Acylations, benzylations, alkylations and sulphonylations giving a wide range of useful products like ketones, alcohols, alkyl aromatics and sulphones are included in this reaction. The petrochemical industry wherein a large number of alkyl hydrocarbons are produced by alkylation reactions is also a beneficiary of this reaction mechanism. The conventional catalysts used in this reaction mechanism include $AlCl_3$, HF, $H_2SO_4$, $BF_3$ and $BPO_4$. Most batch processes use $AlCl_3$ as the soluble acid catalyst since it is a powerful Lewis acid and also inexpensive. However, it is difficult to handle $AlCl_3$ and other similar metal halides since they get easily hydrolysed. Very often these catalysts are required in stoichiometric amounts. A large inventory of these materials pose health, safety and storage problems. The traditional route of liquid phase alkylation using mineral acids and $AlCl_3$ as catalyst suffer from the disadvantage of high capital costs, reactor corrosion, formation of by-products and the difficulty in catalyst regeneration. In recent times, attention is being focused on development of environmentally friendly catalysts for the production of intrinsically important chemicals and chemical intermediates.

The use of safe solid acids in the place of traditional Friedel Crafts catalysts and mineral acids have become important. Several alkylation reactions of aromatic hydrocarbons and functional aromatic hydrocarbons have been tried over zeolites, oxides, mixed oxides and supported oxides. Clays such as montmorillonite with an acidic function are also being considered as alternative catalysts for these reactions. Clays have also been modified for this purpose by pillaring with polyhydroxy metal cations such as Zr, Al, Cr, Ga, etc, acid activation, ion exchange with transition metals and by metal oxide impregnation.

Alkylation of phenols is important in chemicals industries particularly in the agrochemical and pharmaceutical industries. (Fiege et al, in Gerhartz W., et al eds. 1987—Valmann Encyclopedia of Industrial Chemistry, $5^{th}$ edition, Wemheim, VCH Verlagsglsellaschaf; Lowenheim F. A. et al, 1975, Industrial Chemicals, A. Wiley InterScience, New York, Kirk, J., et al, 1981, Encyclopedia of Chemical Technology, $3^{rd}$ edition, Wiley, New York). Alkylation of phenol methanol over various catalysts has been studied (Nozaka et al, Bull. Chem. Soc. Japan, 50, 1997, 614; Narayanan et al, J. Mol. Catal., 52, 1987, 129; Velu et al, React. Kinetic Catal. Lett. 62(2), 1997, 339 and Appl. Catal. A. General, 119, 1994, 241). Karuppanasamy et al report the alkylation of phenol with alcohol over thoria (J. Catal. 63, 1980, 433). Klemm et al report the alkylation of phenol with 2-propanol (J. Org. Chem., 45, 1980, 4326). Alkylation of isopropanol over zeolite catalyst is reported in Guo Changwan et al (Beinjing Huagon Yanjuyuan, 27(3), 1998, 163). Tertiary butylation of phenol was carried out over acid catalyst (Corma et al, J. Catal. 134, 1992, 58 and Appl. Catal. 105, 1993, 271). Peimo et al report the tertiary butylation of phenol over zeolite solid acid catalyst in vapour phase (Huadong Huadong Xueynan Xuebao, 14(4), 1998, 476; See also Chang et al—U.S. Pat. No. 5,288,927 and Kuizhang et al., Appl. Catal. A. General, 166, 1998, 89).

Alkylation of dihydroxy benzene with tertiary butyl alcohol using mineral acids was investigated by Komeev et al (USSR Patent 1583407, 1990).

The prior art processes above suffer from the following disadvantages:
1. Catalyst cannot be reused
2. Disposal of the acids used is not environmentally safe and/or economical
3. The selectivity is frequently observed to be low
4. Corrosion of the reactors and the reaction vessel
5. The process and the reactants are not easily handled
6. Large amounts of catalyst are required It is therefore necessary to develop a process that overcomes the drawbacks enumerated above.

OBJECTS OF THE INVENTION

The main object of the invention is to develop a process for the preparation of dihydroxybenzene which overcomes the drawbacks of the prior art enumerated above.

Another object of the invention is to develop a process for the preparation of alkylated dihydroxybenzene which is safe and economical.

A further object of the invention is to develop a process for the preparation of alkylated dihydroxybenzene wherein the catalyst can be recycled.

Yet another object of the invention is to develop a process for preparation of alkylated dihydroxybenzene wherein the amount of catalyst required is less leading to savings in costs.

These and other objects of the invention are achieved by the process of the invention detailed below.

SUMMARY OF THE INVENTION

Accordingly the present invention provides a process for the preparation of alkylated dihydroxybenzene, said process comprising alkylating dihydroxy benzene with tertiary butyl alcohol in the presence of a catalyst at a temperature in the range of 40 to 90° C. for a time period in the range of 2 to 8 hours, separating the alkylated dihydroxybenzene.

In one embodiment of the invention the dihydroxybenzene is selected from the group consisting of resorcinol, hydroquinone and catechol.

In another embodiment of the invention, the catalyst used is selected from zeolites of the types HZSM-5 ($SiO_2/Al_2O_3=30$), HY ($SiO_2/Al_2O_3=5.2$), H-Mordenite (HM) ($SiO_2/Al_2O_3=20$), MCM-41, Montmorillonite—K10 clay, alumina and polyaniline sulfate.

In another embodiment of the invention, the reaction is carried out at a temperature in the range of 60 to 90° C.

In a further embodiment of the invention, the reaction is carried out for a time period in the range of 6 to 8 hours.

DETAILED DESCRIPTION OF THE INVENTION

The process of the invention uses solid acid or polyaniline sulfate as the catalyst for the alkylation of dihydroxybenzene with tertiary butyl alcohol. The dihydroxybenzene is generally resorcinol, hydroquinone and catechol. Zeolites of the types HZSM-5 ($SiO_2/Al_2O_3=30$), HY ($SiO_2/Al_2O_3=5.2$), H-Mordenite (HM) ($SiO_2/Al_2O_3=20$), MCM-41, Montmorillonite—K10 clay, alumina and polyaniline sulfate are used as the catalyst for the process of the invention.

The reaction is preferably carried out at a temperature in the range of 60 to 90° C. and for a time period in the range of 6 to 8 hours.

The catalyst can be removed by any conventional method such as filtration followed by separation of the alkylated product by conventional column chromatography using adsorbents such as silica gel, alumina and a solvent such as chloroform, ethylacetate, hexane and any mixture thereof. The catalyst can be recycled to the reaction mixture.

The following examples are illustrative and should not be construed as limiting the scope of the invention in any manner.

EXAMPLE 1

2.8 ml of tertiary butyl alcohol was taken in 50 ml round bottom flask and 1 g of resorcinol and 200 mg of catalyst was added. The reaction mixture was refluxed at 80° C. for 8 hours. The reaction mixture was then filtered an the filtrate analysed using a CHEMITO 8510 Gas Chromatography using 20% SE-30 column coupled with flame ionisation detector for product distribution.

Gas Chromatography—Mass spectral fragmentation pattern and Proton Nuclear Magnetic Resonance spectra ($^1$HNMR) of the products proves that the products obtained are a mixture of mono and dialkylated benzene.

Different catalysts used and conversion and selectivities are given in Table 1 below:

TABLE 1 conversion and selectivities using different solid acid catalysts

| Solid acid catalyst | Conversion of resorcinol (%) | Selectivity (%) | |
|---|---|---|---|
| | | 4-t-butyl resorcinol | 4,6-di-tertiary butyl resorcinol |
| HZSM-5 | 6 | 100 | |
| HY | 44 | 77 | 23 |
| HM | 18 | 84 | 16 |
| MCM-41 | 15 | 96 | 4 |
| Montmorillonite-K10 | 3 | 100 | |
| Modified montmorillonite K-10 | 99 | 27 | 73 |

EXAMPLE 2

2.8 ml of tertiary butyl alcohol was taken in 50 ml round bottom flask and 1 g of resorcinol and 200 mg of catalyst was added. The reaction mixture was refluxed at 80° C. for 2, 4, 6 and 8 hours, filtered and the product analysed. The reaction was carried out using modified montmorillonite K10 solid acid catalyst and the conversion and selectivities are given in Table 2 below.

TABLE 2 conversion and selectivity with change in reaction time

| Reaction time (hours) | Conversion of resorcinol (%) | Selectivity (%) | |
|---|---|---|---|
| | | 4-t-butyl resorcinol | 4,6-ditertiary butyl resorcinol |
| 2 | 28 | 86 | 12 |
| 4 | 2 | 46 | 54 |
| 6 | 81 | 58 | 42 |
| 8 | 99 | 27 | 73 |

EXAMPLE 3

2.8 ml of tertiary butyl alcohol was taken in 50 ml round bottom flask and 1 g of resorcinol and 200 mg of catalyst was added. The reaction mixture was refluxed at 80° C. for 8 hours. The temperature of the reaction mixture was varied from 60 to 90° C. in steps of 10° C. The reaction product was filtered and analysed. The reaction was carried out using modified montmorillonite K10 solid acid catalyst and the conversion and selectivities are given in Table 3 below.

TABLE 3 conversion and selectivity with change in reaction temperature

| Temperature of the reaction (° C.) | Conversion of resorcinol (%) | Selectivity (%) | |
|---|---|---|---|
| | | 4-t-butyl resorcinol | 4,6-ditertiary butyl resorcinol |
| 60 | 7 | 100 | |
| 70 | 33 | 84 | 16 |
| 80 | 42 | 79 | 21 |
| 90 | 99 | 27 | 73 |

EXAMPLE 4

2.8 ml of tertiary butyl alcohol was taken in 50 ml round bottom flask and 1 g of resorcinol and 200 mg of catalyst was added. The reaction mixture was refluxed at 80° C. for 8 hours. The mole ratio of resorcinol to tertiary butyl alcohol was varied in the following: 1:3; 1:5, 1:7, and 1:9. The reaction product was filtered and analysed. The reaction was carried out using modified montmorillonite K10 solid acid catalyst and the conversion and selectivities are given in Table 4 below.

TABLE 4 conversion and selectivity with change in molar ratios of resorcinol and tertiary butyl alcohol

| Molar ratio of resorcinol to tertiary butyl alcohol | Conversion of resorcinol (%) | Selectivity (%) | |
|---|---|---|---|
| | | 4-t-butyl resorcinol | 4,6-ditertiary butyl resorcinol |
| 1:3 | 99 | 27 | 73 |
| 1:5 | 33 | 79 | 21 |
| 1:7 | 30 | 80 | 20 |
| 1:9 | 10 | 91 | 9 |

EXAMPLE 5

2.8 ml of tertiary butyl alcohol was taken in 50 ml round bottom flask and 1 g of hydroquinone and 200 mg of modified montmorillonite—K10 catalyst powder was added. The reaction mixture was refluxed at 80° C. for 8 hours. The conversion of hydroquinone was found to be around 57%.

EXAMPLE 6

2.8 ml of tertiary butyl alcohol was taken in 50 ml round bottom flask and 1 g of catechol and 200 mg of modified montmorillonite solid acid catalyst powder was added. The reaction mixture was refluxed at 80° C. for 8 hours. The conversion of catechol was found to be around 45%.

EXAMPLE 7

2.8 ml of tertiary butyl alcohol was taken in 50 ml round bottom flask and 1 g of resorcinol and 200 mg of polyaniline sulfate catalyst was added (for preparation of catalyst see *Composition and spectral studies of polyaniline salts*, S. Palaniappan, *Polymers for Advanced Technology*, 5, 1994, 225). The reaction mixture was refluxed at 80° C. for 8 hours. The reaction mixture was then filtered and the product analysed. The conversion and selectivities are given in Table 5 below.

TABLE 5 conversion and selectivity with change in molar ratios of resorcinol and tertiary butyl alcohol and using polyaniline sulfate catalyst

| Molar ratio of resorcinol to tertiary butyl alcohol | Conversion of resorcinol (%) | Selectivity (%) | |
|---|---|---|---|
| | | 4-t-butyl resorcinol | 4,6-ditertiary butyl resorcinol |
| 1:3 | 51 | 73 | 27 |
| 1:5 | 41 | 34 | 66 |

1. The use of solid acid catalysts or solid polymer catalysts in the liquid phase alkylation of dihydroxy benzene with tertiary butyl alcohol is done for the first time.
2. High catalytic activity and selectivity are observed.
3. The solid acid catalyst does not corrode the reaction vessel.
4. Repeated use of the catalyst is possible allowing recycling of the catalyst to the reaction vessel.
5. The turn over frequency is improved.
6. Separation of the catalyst from the reaction mixture is easy
7. Disposal of the solid acid catalysts is not a problem since they are environmentally safe.

We claim:

1. A process for the preparation of alkylated dihydroxybenzene, said process comprising alkylating dihydroxybenzene with a tertiary butyl alcohol in the presence of a montmorillonite K-10 solid acid catalyst at a temperature in the range of 40 to 90° C. for a time period in the range of 2 to 8 hours, and separating the alkylated dihydroxybenzene.

2. The Process of claim 1 wherein the dihydroxybenzene to be alkylated is selected from the group consisting of resorcinol, hydroquinone and catechol.

3. The process of claim 1 wherein the process is carried out at a temperature between about 60° C. to 90° C.

4. The process of claim 1 wherein the process is carried out for a time period between about 6 to 8 hours.

* * * * *